United States Patent
Jung (10) Patent No.: US 9,675,479 B2
(45) Date of Patent: Jun. 13, 2017

(54) STENT TO BE IMPLANTED WITHIN OR AROUND A HOLLOW ORGAN

(75) Inventor: Johannes Jung, Karlsruhe (DE)

(73) Assignee: PFM MEDICAL AG, Cologne (DE)

( * ) Notice: Subject to any disclaimer, the term of this patent is extended or adjusted under 35 U.S.C. 154(b) by 0 days.

(21) Appl. No.: 10/528,275

(22) PCT Filed: Sep. 16, 2003

(86) PCT No.: PCT/DE03/03067
§ 371 (c)(1),
(2), (4) Date: Aug. 18, 2005

(87) PCT Pub. No.: WO2004/026176
PCT Pub. Date: Apr. 1, 2004

(65) Prior Publication Data
US 2006/0155355 A1 Jul. 13, 2006

(30) Foreign Application Priority Data
Sep. 17, 2002 (DE) .................................. 102 43 136

(51) Int. Cl.
*A61F 2/915* (2013.01)
*A61F 2/91* (2013.01)
*A61F 2/82* (2013.01)

(52) U.S. Cl.
CPC ................ *A61F 2/91* (2013.01); *A61F 2/915* (2013.01); *A61F 2002/825* (2013.01); *A61F 2002/91541* (2013.01); *A61F 2002/91558* (2013.01); *A61F 2230/0054* (2013.01)

(58) Field of Classification Search
CPC .... A61F 2002/9155; A61F 2002/91558; A61F 2002/19566; A61F 2002/19575; A61F 2/915; A61F 2002/91541; A61F 2/91
USPC .... 623/1.1, 1.16, 1.17, 1.18, 1.15–1.2, 1.22, 623/1.3–1.35
See application file for complete search history.

(56) References Cited

U.S. PATENT DOCUMENTS

| | | | |
|---|---|---|---|
| 5,707,386 A * | 1/1998 | Schnepp-Pesch et al. ... | 606/194 |
| 5,922,020 A * | 7/1999 | Klein et al. ................... | 623/1.15 |
| 5,925,061 A * | 7/1999 | Ogi et al. ....................... | 623/1.2 |
| 5,948,016 A | 9/1999 | Jang | |

(Continued)

FOREIGN PATENT DOCUMENTS

| DE | 197 31 021 A1 | 1/1999 |
|---|---|---|
| DE | 197 46 882 A1 | 4/1999 |

(Continued)

*Primary Examiner* — Kathleen Holwerda
(74) *Attorney, Agent, or Firm* — Grossman, Tucker, Perreault & Pfleger, PLLC (57) ABSTRACT

Stents (10) that are implanted within or around a hollow organ, especially self-expanding stents, comprising several annular wall segments (11) which are provided with an elastic structure and are joined to each other by means of connecting elements (12), are often problematic because the length of said stents is modified due to compressive stress, tensile stress, or contraction thereof, potentially resulting in undesired displacement of the stent (10). In order to prevent such positional changes of an implanted stent (10), the inventive connecting elements (12) form at least one continuous longitudinal web (13) which is provided with at least one component in an axial direction for receiving compressive stress or tensile stress in a longitudinal direction.

16 Claims, 5 Drawing Sheets

(56) References Cited

U.S. PATENT DOCUMENTS

| | | | |
|---|---|---|---|
| 6,117,165 A * | 9/2000 | Becker | 623/1.15 |
| 6,203,569 B1 * | 3/2001 | Wijay | 623/1.15 |
| 6,730,117 B1 * | 5/2004 | Tseng et al. | 623/1.16 |
| 7,141,062 B1 * | 11/2006 | Pinchasik et al. | 623/1.15 |
| 7,993,388 B2 * | 8/2011 | Lee et al. | 623/1.15 |
| 2001/0056298 A1 * | 12/2001 | Brown et al. | 623/1.16 |
| 2002/0019660 A1 * | 2/2002 | Gianotti et al. | 623/1.15 |
| 2002/0032478 A1 * | 3/2002 | Boekstegers et al. | 623/1.16 |
| 2002/0042648 A1 * | 4/2002 | Schaldach et al. | 623/1.15 |
| 2002/0058989 A1 * | 5/2002 | Chen et al. | 623/1.15 |
| 2002/0095206 A1 * | 7/2002 | Addonizio et al. | 623/1.15 |
| 2002/0161429 A1 * | 10/2002 | Jang | 623/1.15 |
| 2003/0105517 A1 * | 6/2003 | White et al. | 623/1.17 |
| 2004/0054398 A1 * | 3/2004 | Cully et al. | 623/1.15 |
| 2004/0102834 A1 * | 5/2004 | Nakano et al. | 623/1.15 |

FOREIGN PATENT DOCUMENTS

| | | |
|---|---|---|
| DE | 100 50 940 A1 | 4/2002 |
| EP | 0 928 605 A | 7/1999 |
| WO | WO 96/33671 | 10/1996 |
| WO | WO 99 65418 A | 12/1999 |
| WO | WO 00/47134 | 8/2000 |
| WO | WO 01 89414 A | 11/2001 |
| WO | WO 02 13725 A | 2/2002 |

* cited by examiner

STENT TO BE IMPLANTED WITHIN OR AROUND A HOLLOW ORGAN

The invention concerns a stent for implantation in or around a hollow organ, in particular a self-expanding stent with several ring-shaped wall segments that have an elastic structure and are linked with each other via connector devices.

A stent of this type is described, for example, in DE 197 46 882 A1. Stents are inserted in hollow organs such as blood vessels, urinary ducts, esophagi or bile ducts to ensure that these hollow organs maintain sufficient clearance. Blood vessels are particularly prone to blockage by deposits. This prevents the blood from flowing freely and can have very serious consequences. A stent of this type is therefore inserted into a diseased hollow organ via a catheter. In addition, self-expanding stents are, for example, often used which are in a first phase inserted into the hollow organ at a small diameter and in a second phase are expanded or expand by themselves from this position at larger diameter. However, stents are also used if a hollow organ such as a blood vessel no longer has sufficient strength to maintain its original shape, resulting in a so-called aneurysm. In this case there is the risk that the hollow organ, the blood vessel in this case, expands and may tear at such a diseased spot, leading to internal bleeding. To prevent such internal injury, a stent, in particular a coated stent, is inserted into the diseased vessel in such a way that the stent bridges expanded, aneurysmatically altered segment. The two ends of the stent thereby seal the healthy segments before and after.

Such a stent must have sufficient flexibility to be able to follow the movements of its carrier or the blood vessels or hollow organs, but it is also necessary, especially with self-expanding stents, that the stent be compressed to the small diameter in the first phase and that it then be able to expand to the large diameter in the second phase. Linking several elastic, ring-shaped wall segments to each other via individual connector devices ensures this flexibility. The disadvantage of the stent known from DE 19746882 A1 is that a contraction, such as when it is introduced into the vessel, leads to a change in length of the stent. This may occur, for example, if the stent is used under tensile stress and subsequently shortens, with the possibility that the stent no longer covers the narrowed or expanded segment. Another danger is that the tip of the stent being subjected to tensile stress protrudes from the treated vessel if, for example, a change occurs in a branch-off vessel.

The purpose of the invention is therefore to offer a stent that is flexible and yielding, but one that shows only a small change in length or none at all in case of a tensile stress or compressive stress or as a result of a contraction.

The invention achieves this purpose by the fact that the connector devices in a stent of the type mentioned in the introduction form at least one continuous longitudinal flange that has at least one component in the axial direction to absorb the compressive strength or tensile strength in the longitudinal direction, thereby keeping its length essentially constant.

In this way the stent consists, on the one hand, of elastic, ring-shaped wall segments, allowing it to follow the movements of the hollow organ in which it is implanted. On the other hand, the individual wall segments are linked with each other via a continuous longitudinal flange that is able to absorb compressive stress or tensile stress in the longitudinal direction without causing the stent to change in length. By the same token, a contraction, thus compression of the individual wall segments, does not cause the stent to change its length either because any tensile stress or compressive stress that may occur is transmitted to and absorbed by the continuous longitudinal flange and.

Another embodiment of the invention is characterized by the fact that the wall segments have alternatively a first set of spring devices and a second set of spring devices mounted at an angle to each other. This gives the wall segments a zigzag-like, elastic structure allowing for a good, elastic spring effect.

The spring devices are preferably more or less rectilinear. This rectilinear design has to be understood with reference to a projection onto the exterior surface area of the stent.

The connector devices link either only first or only second spring devices with each other, thereby forming a more or less straight line. The connector devices themselves are not elastic with regard to the compressive and tensile forces exerted along the longitudinal axis of the stent and are essentially rigid, i.e. they absorb the compressive and tensile forces together with the spring devices that link them and thereby prevent the stent from changing in length. In this way, the linked first and second spring devices form, together with the connector devices, the continuous longitudinal flange. For this purpose, all connector devices and the spring devices linked with them should be arranged in parallel to each other, i.e. they lie inside a stent in a more or less straight line. If the stent has more than one connecting flange, the individual flanges do not cross or touch each other but instead run parallel at a certain distance from each other. This also refers to the projection onto a peripheral area of the stent. This ensures that the introduced force is exerted only along the longitudinal flange and has no cross component that could lead to an undesirable shortening or lengthening of the stent.

One embodiment of the invention is characterized by several longitudinal flanges parallel to each other in a projection to an exterior peripheral area that are arranged at a certain distance from each other in the direction of the periphery.

These might be, for example, three of four longitudinal flanges. In this way, the wall segments are positioned very effectively in relation to each other, thereby also reliably preventing a change in length of the stent.

It is also possible for the longitudinal flange to have a helical or spiral-shaped shape and wind axially around the wall of the stent. This may be the case if, for example, the longitudinal flange consists of the connector devices and the first and second spring devices linked with them, resulting in a particularly simple design. Changes in length because of compressive stress or tensile stress, or because of compaction of the stent, are nevertheless reliably prevented within the framework of the forces exerted during use.

The connector devices may also have a greater material thickness or width than the spring devices, especially in relation to the wall areas. Costs are reduced in particular if a self-expanding stent is excised via laser from a tube-shaped body with small diameter. In the first, small-diameter phase, the connector devices are, for example, slightly S-shaped. In the second, larger-diameter phase, the connector devices feature at least one component parallel to the longitudinal flange. The connector devices may be, for example, twice as wide as the spring devices, resulting in a particularly simple cutting pattern. Normally, but not necessarily, the connector devices are shorter than the spring devices and have a useful length of not more than ¾, preferably not more than ⅔ of the length of the spring device. Special preference is given to lengths of half the spring length or less.

The stent is preferably designed in one piece, allowing for a stable construction without unnecessary edges or possible breakpoints.

The material used for the stent may be a shape memory material such as a so-called memory metal like a nickel titanium alloy as commercially available under the name Nitinol. According to the invention, even polymers as used in other areas of medical science for implants in the body are suitable for the manufacture of stents. For example, a suitable cutting pattern for making the spring devices and connector devices can be cut from a tube-shaped body with a small diameter via laser. This expanded form can then be imprinted on the tube-shaped body in the known manner. If the stent produced in this way is then compressed in the small-diameter phase and is inserted into, for example, a diseased blood vessel via a catheter, the stent can then in position be automatically returned to its imprinted form by heating it above the so-called conversion temperature.

Other materials suitable for stents are stainless steel, plastic or so-called self-dissolving materials. These self-dissolving materials are above all of advantage if a stent is not meant to be permanent. If self-expanding stents not are used, they can be expanded at the desired position via a balloon catheter, for example.

Preferably, the surface of the stent is refined, smoothed and/or polished, resulting in a smooth and body-compatible surface.

Following is an example of embodiment of the invention, explained using the following illustrations.

Figure 1:
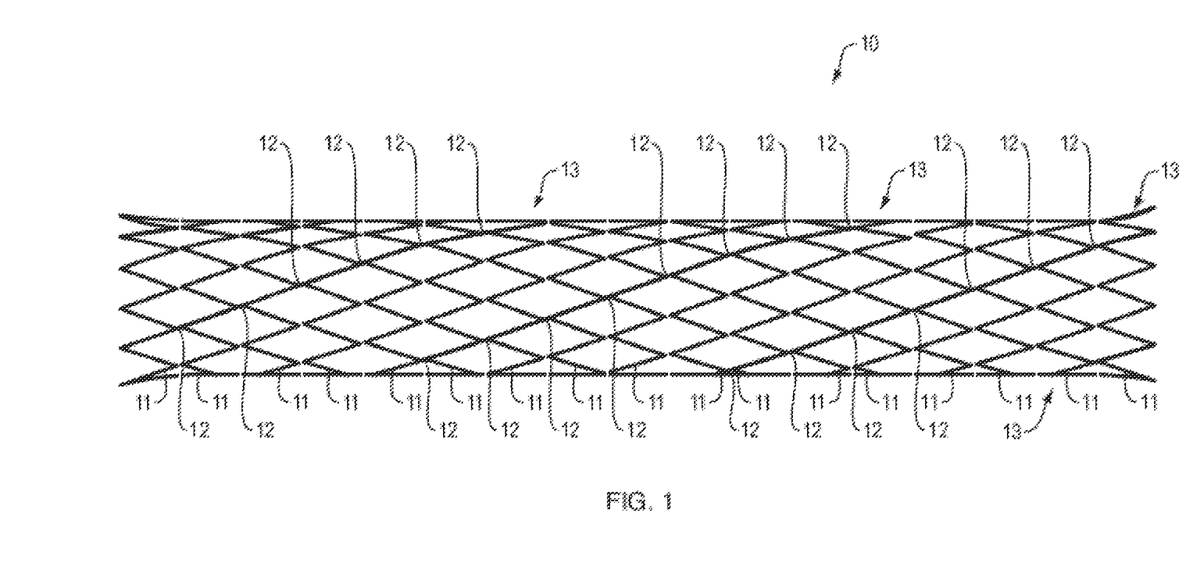
FIG. 1 a stent with the characteristics of the invention.

FIG. 1 shows a top view of a stent 10 with the characteristics of the invention. The stent 10 as shown is a so-called flexible stent that is highly flexible, especially in the radial direction, in order to be able to follow the movements of the hollow organ into which it is inserted. The stent 10 overall has a tube-shaped design and has several wall segments 11 with elastic structures. All the wall segments 11 in FIG. 1 have a zigzag-shaped structure that will be explained in more detail below.

Adjoining wall segments 11 are linked with each other via connector devices 12. The connector devices 12, as depicted in FIG. 1, are arranged in such a way that several connector devices 12 following each other and communicating between first spring devices 14, form a common continuous uninterrupted longitudinal flange 13 communicating from a first end to the second end of the formed stent 10. FIG. 1 shows a total of four continuous longitudinal flanges 13 extending more or less helically across the stent 10.

Tensile stress and compressive stress are passed from one wall segment 11 to the next wall segment 11 along the substantially axially aligned connector devices 12 shown in FIG. 1 and thus is deflected along the continuous uninterrupted longitudinal flange 13. Since these longitudinal flanges 13 are formed by the substantially aligned connector devices 12 which are substantially axially aligned with adjoining first spring devices 14, the flanges 13 run in a straight line in relation to a projection onto the external peripheral area of the stent 10. As a consequence of the aligned connector devices 12 and aligned first spring devices 14, no cross components occur in case of tensile stress or compressive stress. Thus, any compressive stress or tensile stress that does occur, as well as the compaction of the stent 10, does not change its length.

Figure 2:
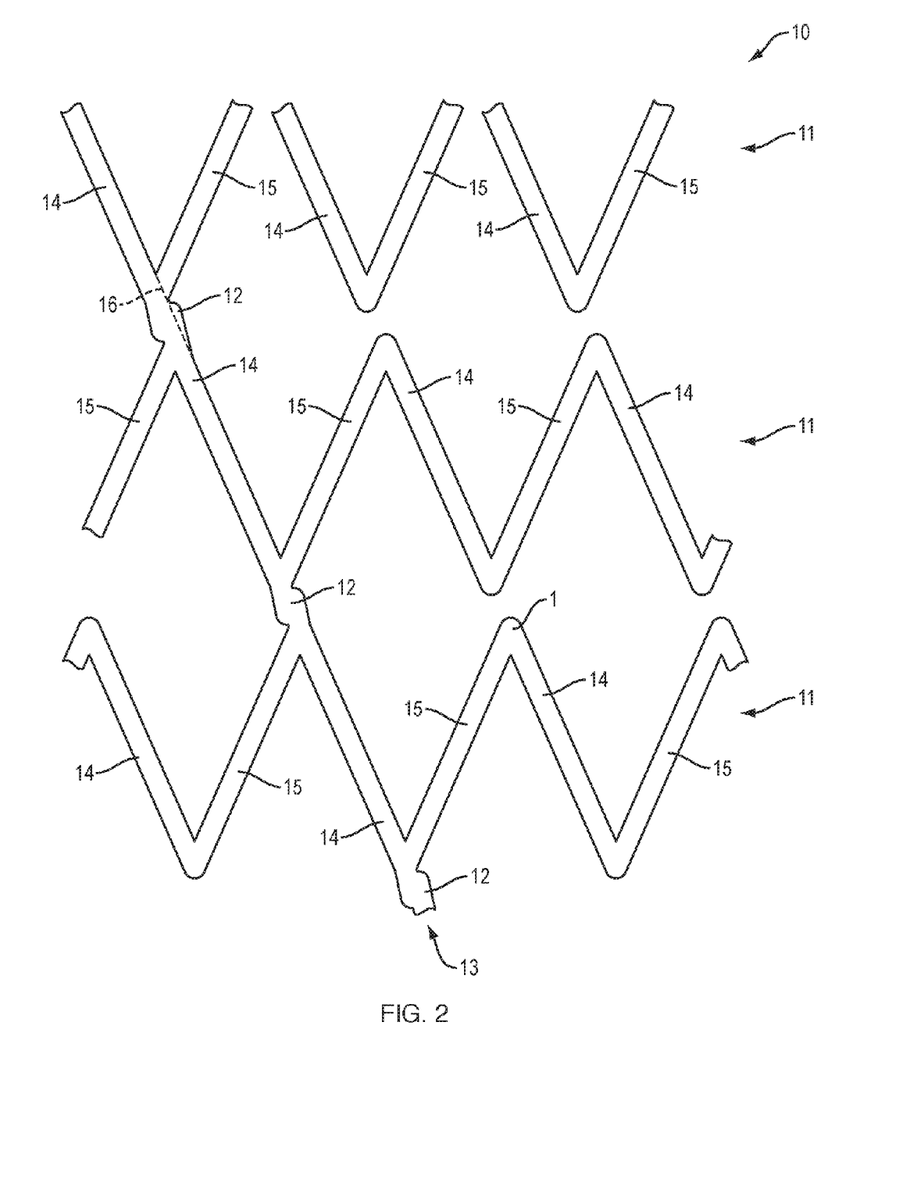
FIG. 2 an enlarged partial view of the stent of FIG. 1.

FIG. 2 shows an enlarged partial view of the stent 10 of FIG. 1. As the illustration shows, the wall segments 11 have both first spring devices 14 and second spring devices 15. The first spring devices 14 and the second spring devices 15 are at an angle to each other. In this way, the first spring devices 14 and the second spring devices 15 form a zigzag-like structure, giving the wall segments 11 a resilient and yielding design in the radial direction.

As FIG. 2 also shows, the connector devices 12 link spring devices 14 of the individual wall segments 11 that are adjacent to each other, forming thereby the longitudinal flanges 13 together with the first spring devices 14 linked via these connector devices 12. The individual wall segments 11 are displaced in the illustration from the adjoining wall segments 11 by an offset that has more or less the thickness of the first spring device 14 and the second spring device 15 combined. The connector devices 12 have more or less an S-shaped structure, resulting in a direction of force 16 more or less parallel to the first spring devices 14 from a first spring device 14 to a first spring device 14 adjacent to it. The connector devices 12 also are approximately twice as thick as the first spring devices 14. If in this case the force exerted from the first spring 14 to the first spring 14 adjacent to it is not perfectly parallel to their lengthwise direction, any occurring cross forces can be absorbed, to a certain degree, by this thickened design of the connector devices 12 without leading to a change in the length of the stent 10.

Figure 3:
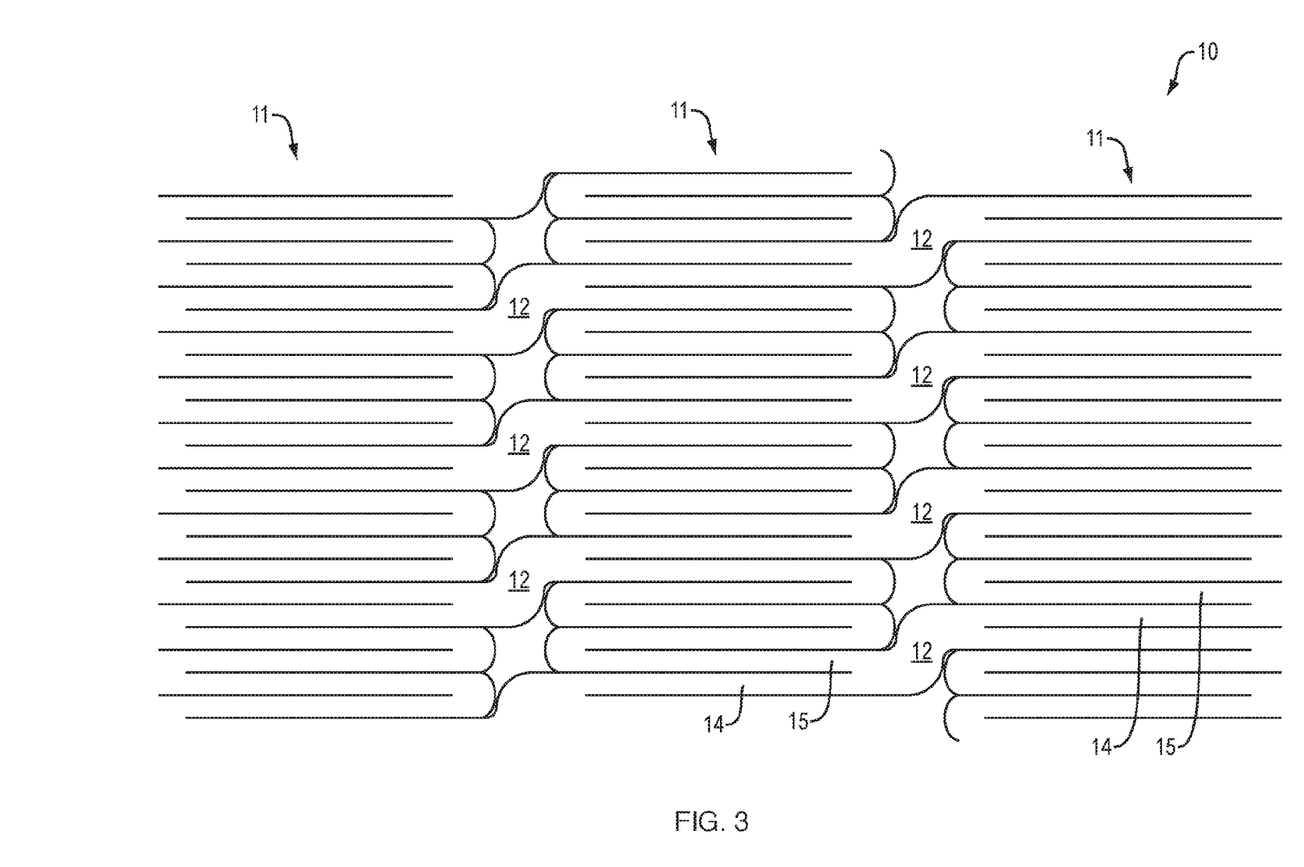
FIG. 3 a schematic view of a cutting pattern for manufacturing stents with the characteristics of the invention, FIG. 4 a schematic view of a projection of the wall segments and the connector devices onto the external peripheral area of the stent and FIG. 5 a schematic view similar to FIG. 4 of another stent with the characteristics of the invention.

FIG. 3 shows a schematic view of a cutting pattern for manufacturing a stent 10 that has not yet expanded. The stent 10 is cut from a small tube made of a suitable material, for example a shape memory material such as a memory metal like Nitinol, via a laser. FIG. 3 shows an enlarged partial view of a cutting pattern in the unwound state projected onto the peripheral area of the stent. For the sake of simplification, only two first spring devices 14 and two second spring devices 15 are identified as such in FIG. 3. As the figure shows, in a first phase after cutting the pattern into the small tube made of for example memory metal, the first spring devices 14 and the second spring devices 15 are adjoining each other. The first spring devices 14 and the second spring devices 15 adjacent to them are parallel to each other. The figure shows clearly the S-shaped design of the connector devices 12. FIG. 3 also makes clear that wall segments 11 adjoining each other are displaced against each other by an offset having the thickness of the first spring 14 and the second spring 15. In this way, in the first phase the ends of a first spring device 14 of a wall segment 11 are linked via connector devices 12 with a first spring device 14 of the adjoining wall segments 11 displaced by the offset. After cutting the pattern shown in FIG. 3 into a tube-shaped blank made of memory metal, the stent manufactured in this way is expanded in a second phase that has a larger diameter than the first phase. This second phase is then imprinted on the stent in the known manner. For implantation via a catheter, the stent 10 prepared in this manner is then compressed into a small-diameter phase. After being positioned as desired, the stent 10 can then be expanded again into the imprinted form of the second phase by heating it above the so-called conversion temperature. However, it is also possible to expand the stent 10 via a balloon catheter.

Figure 4:
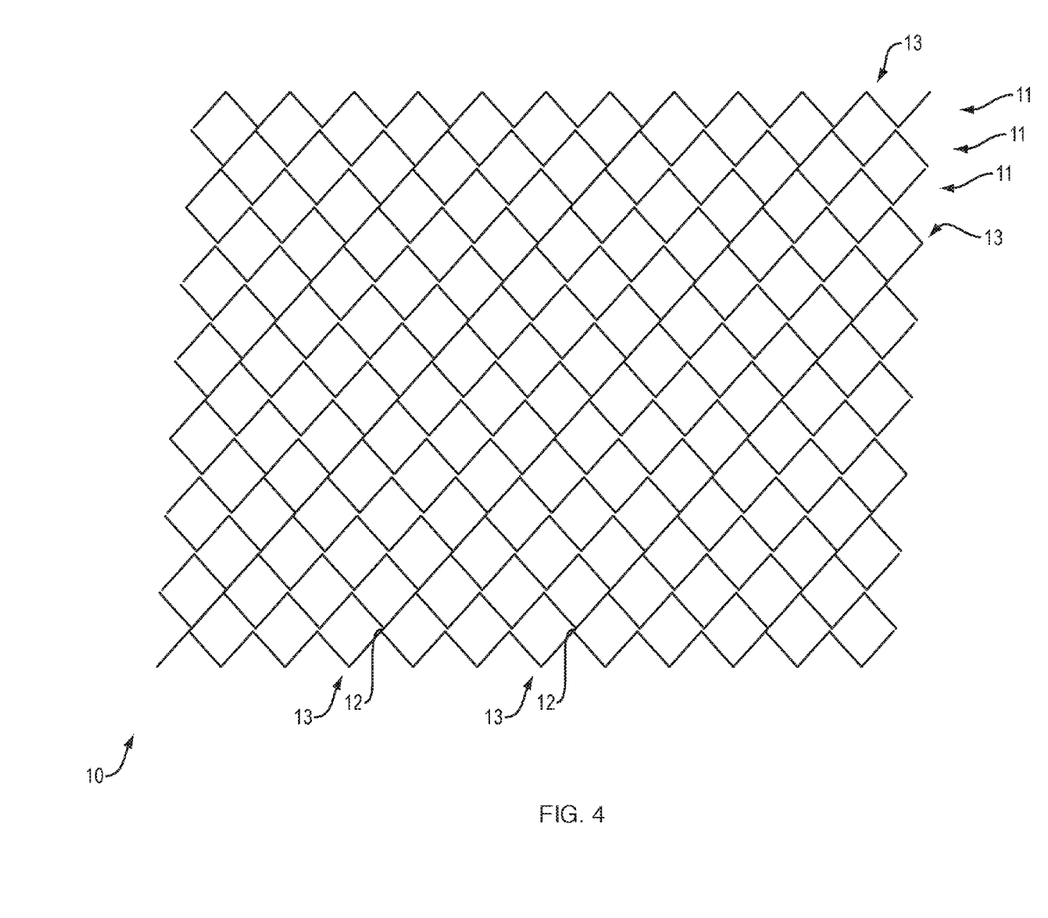

FIG. 4 shows a schematic view of a projection of the wall segments 11 and the connector devices 12 onto the exterior peripheral area of the stent 10. The illustration shows clearly the zigzag design of the individual wall segments 11. For a better view, the illustration identifies only three wall segments 11. FIG. 4 also clearly shows the longitudinal flanges 13 formed by the first spring devices 14 and connector devices 12 alternatively following each other. For a better view, only two longitudinal flanges 13 and two connector devices 12 are identified as such in the illustration. The connector devices 12 are shown in the illustration as bulges. The connector devices 12 may for example also be spot weldings.

Figure 5:
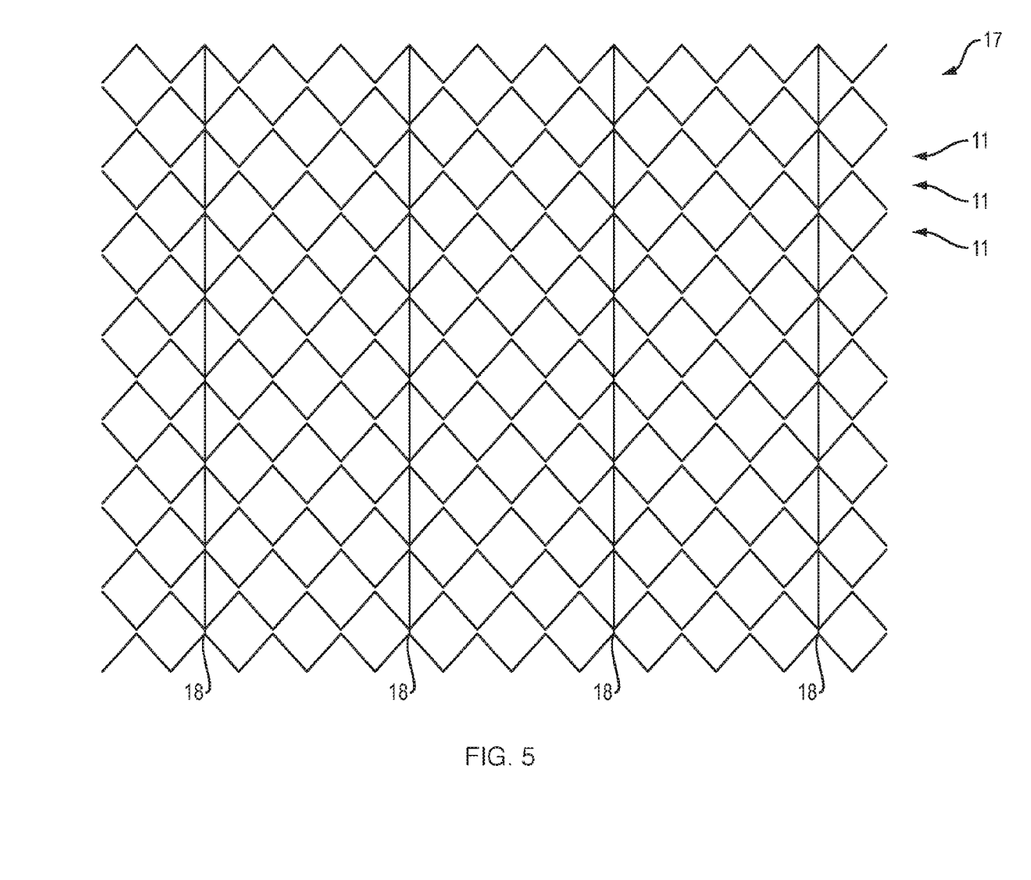

FIG. 5 shows a schematic view similar to FIG. 4 of another stent 17 with the characteristics of the invention. The same elements have the same identifiers as in stent 10. For a better view, only three wall segments 11 are identified as such in FIG. 5. The stent 17 has axially extending longitudinal flanges 18. FIG. 5 shows four longitudinal flanges 18. The stent 17 is more resistant against compressive stress and tensile stress in the longitudinal direction than the stent 10. However, manufacturing the stent 17 is somewhat more costly and the stent 17 is also somewhat less flexible.

| Campus Medizin und Technik GmbH | CAM 8664 PCT TMF/fo |
|---|---|

Stent for Implantation in or Around a Hollow Organ

Identifiers

10 Stent
11 Wall segment
12 Connector device
13 Longitudinal flange
14 First spring device
15 Second spring device
16 Direction of exerted force
17 Stent
18 Longitudinal flange

What is claimed is:

1. A stent for implantation in or around a hollow organ, comprising:
    a first end, a second end, and a plurality of adjacently positioned ring shaped elastic wall segments along a length of said stent between said first end and said second end, each wall segment having a radial elastic structure and comprising a plurality of reverse bends with each reverse bend formed of first and second spring devices;
    gaps separating said wall segments;
    rigid connector devices upon each of said wall segments, said connector devices being in communication across said gaps to link only adjacently positioned first spring devices or only adjacently positioned second spring devices, said connector devices having a design such that, in a non-expanded configuration, the adjacently positioned first spring devices or the adjacently positioned second spring devices are displaced from a first wall segment to a second adjacent wall segment with regard to a longitudinal axis of said stent by an offset having a width equal to the thickness of said first and second spring devices combined;
    wherein:
    said connector devices have a length that is less than or equal to one half of a length of said first and second spring devices; and
    a series of said connector devices and the adjacently positioned first spring devices or the adjacently positioned second spring devices are substantially axially aligned with one another along said stent, either end to end or along their longitudinal axes, to form a plurality of continuous longitudinally rigid flanges extending uninterrupted and in a substantially straight line between said first and second end, each of said plurality of continuous longitudinal flanges consisting of respective connector devices and only respective adjacently positioned first spring devices or only respective adjacently positioned second spring devices located upon adjoining wall segments; and
    the plurality of continuous longitudinally rigid flanges less than the plurality of reverse bends of each of the adjoining wall segments.

2. A stent according to claim 1, wherein
    said first spring devices and said second spring devices are arranged in alternate fashion at an angle to each other.

3. A stent according to claim 2, wherein the first spring devices and the second spring devices are substantially rectilinear.

4. A stent according to claim 3, wherein said plurality of continuous longitudinal flanges are parallel to each other in a projection onto an external periphery area of said stent arranged in a direction of the external periphery, and are spaced apart from one another.

5. A stent according to claim 2, wherein said plurality of continuous longitudinal flanges are parallel to each other in a projection onto an external periphery area of said stent arranged in a direction of the external periphery, and are spaced apart from one another.

6. A stent according to claim 2, wherein said first spring devices and said second spring devices have a substantially equal width.

7. A stent according to claim 1, wherein said plurality of continuous longitudinally rigid flanges are parallel to each other in a projection onto an external periphery area of said stent arranged in a direction of the external periphery, and are spaced apart from one another.

8. A stent according to claim 7 wherein the said external periphery is machined to a smooth or polished surface.

9. A stent according to claim 1, wherein said stent may be self expanded for a deployment in said organ.

10. A stent according to claim 1, wherein said stent is made of stainless steel, plastic or a self-dissolving material.

11. A stent according to claim 1 wherein said plurality of continuous longitudinally rigid flanges further comprises three or four continuous longitudinally rigid flanges.

12. A stent for implantation in or around a hollow organ, comprising:
    a unitary structure of a shape memory material, said unitary structure being expandable upon deployment in said organ;
    wherein:
    said unitary structure comprises a tube shaped body defined by a sidewall surrounding an axial interior along a length, said sidewall having voids formed therein defining a plurality of adjacently positioned ring shaped elastic wall segments, each ring shaped elastic wall segment having a radial elastic structure;
    each of said plurality of elastic wall segments comprising a plurality of reverse bends with each reverse bend formed of first and second spring devices arranged in alternate fashion at an angle to each other; and said voids define gaps separating adjacent wall segments of said plurality of wall segments; and said stent further comprises longitudinally rigid connector devices in communication across said gaps linking only adjacently positioned and substantially aligned first spring devices or only adjacently positioned and substantially aligned second spring devices of said wall segments, said connector devices having a design such that, in a non-expanded configuration, the adjacently positioned and substantially aligned first spring devices or the adjacently positioned and substantially aligned second spring devices are displaced from a first wall segment to a second adjacent wall segment with regard to a longitudinal axis of said stent by an offset having a width equal to the thickness of said first and second spring devices combined;

wherein:

said connector devices have a length that is less than or equal to one half of a length of the first and second spring devices; and a series of said connector devices and the adjacently positioned and substantially aligned first spring devices or the adjacently positioned and substantially aligned second spring devices are substantially aligned, either end to end or along their longitudinal axes, along a length of said body between a first of said ring shaped elastic wall segments at one end of said body to a last of said ring shaped elastic wall segments at an opposite end of said body, so as to form a plurality of continuous uninterrupted longitudinally rigid flanges comprised of said connector devices and only respective adjacently positioned and substantially aligned first spring devices or only respective adjacently positioned and substantially aligned second spring devices, each of the plurality of continuous uninterrupted longitudinally rigid flanges extending in a substantially straight line; and the plurality of continuous longitudinally rigid flanges less than the plurality of reverse bends of each of the adjacent wall segments.

13. A stent according to claim 12 wherein said unitary structure is expandable upon a deployment in said organ using a balloon catheter.

14. A stent according to claim 12 wherein said plurality of continuous longitudinally rigid flanges further comprises three or four continuous longitudinally rigid flanges.

15. A stent for implantation in or around a hollow organ, comprising:

a first end, a second end, and a plurality of adjacently positioned ring shaped elastic wall segments along a length of said stent between said first end and said second end, each wall segment having a radial elastic structure and comprising a plurality of reverse bends with each reverse bend formed by first and second spring devices;

gaps separating said wall segments;

connector devices between each of said wall segments, said connector devices being in a communication across said gaps to link only adjacently positioned first spring devices or only adjacently positioned second spring devices, said connector devices having a design such that, in a non-expanded configuration, the adjacently positioned first spring devices or the adjacently positioned second spring devices are displaced from a first wall segment to a second adjacent wall segment with regard to a longitudinal axis of said stent by an offset having a width equal to the thickness of said first and second spring devices combined;

wherein:

a series of said connector devices and the adjacently positioned first spring devices or the adjacently positioned second spring devices are substantially rectilinear with one another along a longitudinal length of said stent to form a plurality of continuous longitudinal flanges, each of said plurality of flanges consisting of respective connector devices and only respective adjacently positioned first spring devices or only respective adjacently positioned second spring devices located upon adjoining wall segments; and wherein said connector devices have a length that is less than or equal to one half of a length of the first and second spring devices; and said flanges preserves the longitudinal length of the stent essentially constant under tensile or compressive stress; and the plurality of continuous longitudinal flanges less than the plurality of reverse bends of each of the adjoining wall segments.

16. A stent according to claim 15 wherein said plurality of continuous longitudinal flanges further comprises three or four continuous longitudinal flanges.

* * * * *